United States Patent
Oka et al.

(10) Patent No.: US 8,730,471 B2
(45) Date of Patent: May 20, 2014

(54) DUV-UV BAND SPECTROSCOPIC OPTICAL SYSTEM AND SPECTROMETER USING SAME

(75) Inventors: Keiko Oka, Yokohama (JP); Yasuhiro Yoshitake, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 207 days.

(21) Appl. No.: 13/145,942

(22) PCT Filed: Dec. 17, 2009

(86) PCT No.: PCT/JP2009/006963
§ 371 (c)(1),
(2), (4) Date: Jul. 22, 2011

(87) PCT Pub. No.: WO2010/097880
PCT Pub. Date: Sep. 2, 2010

(65) Prior Publication Data
US 2011/0279820 A1  Nov. 17, 2011

(30) Foreign Application Priority Data
Feb. 26, 2009  (JP) .................................. 2009-044231

(51) Int. Cl.
*G01J 3/28*  (2006.01)

(52) U.S. Cl.
USPC ......................................................... 356/326

(58) Field of Classification Search
USPC .................. 356/300–334, 402–425, 451–456
See application file for complete search history.

(56) References Cited

U.S. PATENT DOCUMENTS

| | | | |
|---|---|---|---|
| 3,573,456 A * | 4/1971 | Beeh ............................. 250/475.2 |
| 4,999,495 A * | 3/1991 | Miyata et al. ...................... 850/3 |
| 6,335,787 B1 * | 1/2002 | Nishi ................................ 355/67 |
| 6,362,923 B1 | 3/2002 | Lange et al. |
| 6,639,739 B1 * | 10/2003 | Stone et al. .................... 359/793 |
| 7,286,207 B2 * | 10/2007 | Nolscher et al. ................ 355/55 |
| 7,324,274 B2 * | 1/2008 | Komatsu et al. .............. 359/391 |
| 2010/0128278 A1 * | 5/2010 | Deck et al. ..................... 356/477 |

FOREIGN PATENT DOCUMENTS

| | | |
|---|---|---|
| JP | 61-090115 | 5/1986 |
| JP | 3288441 | 6/2002 |
| JP | 2003-527636 | 9/2003 |
| JP | 2003-527636 A | 9/2003 |
| JP | 2004-354556 | 12/2004 |

(Continued)

*Primary Examiner* — Kara E. Geisel
*Assistant Examiner* — Maurice Smith
(74) *Attorney, Agent, or Firm* — McDermott Will & Emery LLP

(57) ABSTRACT

Disclosed are a spectroscopic optical system and a spectrometer both enabling vertical illumination by means of an optical system using only refractive lenses and enabling wide-band color correction in the DUV-UV (190 to 400 nm) range. The spectroscopic optical system and spectrometer each comprise a light source (100), a folding mirror (110), a field stop (120), an object-side focusing lens system (130) for focusing light onto a sample, an image-side focusing lens (140) disposed on the image forming plane of the object-side focusing lens system, and a spectroscope (150) for dispersing regularly reflected light from the sample. The object-side focusing lens system (130) and the image-side focusing lens system (140) are each a spectroscopic optical system corrected with respect to color in a broad band of wavelength from 190 to 400 nm and configured from only refractive lenses enabling vertical illumination. The working distance (WD) of each lens is set shorter than a predetermined distance, and the doublet interval (D) is set longer than a predetermined distance.

9 Claims, 13 Drawing Sheets

(56) References Cited

FOREIGN PATENT DOCUMENTS

| JP | 2004-354556 A | 12/2004 |
| JP | 2005-127830 | 5/2005 |
| JP | 2005-127830 A | 5/2005 |
| JP | 2008-090051 | 4/2008 |
| WO | WO 01/69298 A1 | 9/2001 |
| WO | 2005/040719 A1 | 5/2005 |
| WO | WO 2005/040719 A1 | 5/2005 |

* cited by examiner

{ NUMBER OF LENSES : N
MARGINAL RAY HEIGHT OF EACH LENS : $h_i$
MARGINAL RAY HEIGHT OF LAST LENS : $h_N$
DISTANCE FROM LAST LENS SURFACE TO OBJECT SURFACE : $s_N$
REFRACTIVE POWER AND ABBE NUMBER OF EACH LENS : $\phi_i, \nu_i$

DUV-UV BAND SPECTROSCOPIC OPTICAL SYSTEM AND SPECTROMETER USING SAME

RELATED APPLICATIONS

This application is the U.S. National Phase under 35 U.S.C. §371 of International Application No. PCT/JP2009/006963, filed on Dec. 17, 2009, which in turn claims the benefit of Japanese Application No. 2009-044231, filed on Feb. 26, 2009, the disclosures of which Applications are incorporated by reference herein.

TECHNICAL FIELD

The present invention relates to a spectroscopic optical system and a spectrometer. More particular, the present invention relates to a spectroscopic optical system and a spectrometer that are color corrected for a broad range of wavelengths from deep ultraviolet (DUV) to ultraviolet (UV) (190 to 400 nm) by an arrangement of optical systems using only refractive lenses capable of vertical illumination.

BACKGROUND ART

In the defect detection of sample surface structure, there is an increasing need for spectroscopic measurement using a broad range of wavelengths in the highly sensitive DUV-UV region (from 190 to 400 nm). At this time, lens systems must be color corrected when a broad range of wavelengths and a plurality of wavelengths are used. There are two methods of color correction, one using a reflective optical system and the other using a refractive optical system.

As an example of the reflective optical system, Japanese Unexamined Patent Application Publication (JP-A) No. 2005-127830 (Patent Literature 1) describes a spectroscopic optical system provided with a color corrected lens system of Schwarzschild type for ultraviolet region.

As an example of the refractive and diffractive optical system, JP-A No. 2008-90051 (Patent Literature 2) describes an optical system that is color corrected with respect to an ultraviolet wavelength λ and a wavelength 2λ that is twice the wavelength λ, using diffractive optical element.

As an example of the refractive optical system, Japanese Patent No. 3288441 (Patent Literature 3) describes near-ultraviolet objective lenses that are color corrected for wavelengths over 350 nm in the near ultraviolet to visible region to have the same focal positions, allowing high resolution observation with near ultraviolet light as well as ultraviolet-fluorescent confocal imaging. Further, JP-A No. Sho 61-90115 (Patent Literature 4) describes image-forming objective lenses using fluorite and quartz as lens materials, which are color corrected in a wide range from the ultraviolet at a wavelength of about 200 nm to infrared region.

CITATION LIST

Patent Literature

Patent Literature 1: JP-A No. 2005-127830
Patent Literature 2: JP-A No. 2008-90051
Patent Literature 3: Japanese Patent No. 3288441
Patent Literature 4: JP-A No. Sho 61-90115

SUMMARY OF INVENTION

Technical Problem

The optical system described in Patent Literature 1 is a reflective type and capable of wide-range color correction. However, the reflective-type color corrected optical system illuminates the sample surface at an oblique angle. There is no problem with oblique illumination when the sample surface remains stationary. However, a problem arises when the entire sample surface is continuously scanned by rotating the sample surface. In FIG. 3, when an oblique illumination 811 is applied to continuously scan the sample surface, the sample surface moves vertically (sample surface 1, 1') due to continuous scanning, and the scan target position is displaced (scan target position 821, 831).

Meanwhile, the refractive-diffractive optical system and the refractive optical system, which are described in Patent Literatures 2 to 4, are designed to be capable of vertical illumination. FIG. 4 shows the state in which displacement due to vertical movement of the sample surface is small in vertical illumination. In FIG. 4, vertical illumination 812 is applied to continuously scan the sample surface. In this case, even if the sample surface moves vertically (sample surface 1, 1') due to continuous scanning, the displacement of the scan target position is small (scan target position 822, 832). However, the refractive-diffractive optical system descried in Patent Literature 2 is capable of two-wavelength color correction only for the ultraviolet wavelength λ and the wavelength 2λ that is twice the wavelength λ, and it does not supports wide-range color correction.

The refractive optical system described in Patent Literature 3 does not support color correction for wavelengths including highly sensitive deep ultraviolet wavelengths below 350 nm in the defect detection of sample surface structure.

The refractive optical system described in Patent Literature 4 does not support doublet attachment, which poses a problem in the ultraviolet region. In general, UV curing agent (adhesive) is used for the attachment of doublets. The UV curing agent is cured by irradiating it with ultraviolet light. Thus, when the refractive optical system formed by doublets using UV curing agent is continuously irradiated with ultraviolet light, the portion of the UV curing agent is degraded. At this time, the emitted gas is attached again to the lens surface, and thus the transmittance is reduced. There is another method of attaching doublets without using the UV curing agent to prevent the degradation of quality. However, in the case of attachment, the air space is reduced and uneven brightness (the irregularity in the amount of light) occurs due to interference.

It is desirable to provide a spectroscopic optical system and a spectrometer using the spectroscopic optical system, which are capable of vertical illumination with little influence of sample surface movement, achieving color correction in a wide range of DUV-UV wavelengths (190 to 400 nm).

Other objects, advantages and novel features of the present invention will be apparent from the following detailed description and the drawings attached hereto.

Solution to Problem

Representative ones of the inventions disclosed in the present application will be explained in brief as follows.

A spectroscopic optical system according to the present invention includes: an illumination optical system including a light source, a folding mirror, a field stop, and an object-side objective lens system for illuminating a sample; a detection optical system including the object-side objective lens system, the field stop, the folding mirror, and an image-side focusing lens system disposed on an image forming plane on the object side; and a spectroscope for separating specularly reflected light from the sample. The object-side objective lens system and the image-side focusing lens system are color corrected in a broad range of wavelengths from 190 to 400 nm, and are formed by only refractive lenses. The working distance (WD) of each lens is set so as to satisfy WD≤10.0 mm. In this configuration, the color correction in the DUV-UV region can be achieved.

In the spectroscopic optical system according to the present invention, a distance D of each doublet is set to $(\lambda 1 \cdot \lambda 2)/(4n\gamma) \leq D$ taking into account one reflection.

Here, n is the refractive index of air and $\gamma$ is the spectroscopic resolution. It is also assumed that $\lambda 2$ is the wavelength to be studied, which is determined by selecting the longest wavelength of all the wavelengths in the range to be studied, and $\lambda 1$ is obtained by adding the spectroscopic resolution $\gamma$ to the target wavelength $\lambda 2$.

This makes it possible to prevent the occurrence of uneven brightness (irregularity in the amount of light) due to interference. It is to be noted that when taking into account the case of multiple reflection, the doublet distance D is made 1.5 times the value of one reflection.

Further, in the spectroscopic optical system according to the present invention, the illumination optical system is designed to vertically illuminate the sample. Thus, it is possible to reduce the displacement due to defocusing in high speed and continuous detection.

A spectrometer according to the present invention includes: the spectroscopic optical system; a stage part on which a sample placed, capable of moving a position of the sample relative to the spectroscopic optical system; a control unit for controlling the operation of a spectroscope and the stage part; and a data processing unit for detecting a shape or abnormal shape of patterns formed on the sample, based on the spectral intensity distribution detected by the spectroscope.

Further in the spectrometer according to the present invention, the data processing unit includes a database for storing graphs of the wavelength dependence of the spectral reflectance that is calculated in advance for a different pattern shape in the sample. The data processing unit obtains a graph of the wavelength dependency of the spectral reflectance that is measured for the sample, based on the spectral intensity distribution detected by the spectrometer. Then, the data processing unit selects the one that matches the graph of the wavelength dependence of the spectral reflectance that is measured for the sample, from the graphs of the wavelength dependence of the spectral reflectance that are stored in the database, by means of comparison of waveforms of the spectral reflectance. In this way, it is designed to identify the pattern shape formed on the sample. Note that the pattern shape also includes the film thickness.

Advantageous Effects of Invention

The effect obtained by a typical one of the inventions disclosed in the present application will be described as follows.

According to the present invention, it is possible to perform color correction in a broad range of DUV-UV wavelengths (190 to 400 nm). Further, it is possible to prevent the occurrence of uneven brightness (irregularity in the amount of light) due to interference. In addition, it is capable of vertical illumination, thereby reducing the displacement due to defocusing in high speed and continuous detection, which has been a problem in the oblique illumination of the existing reflection optical system. These features enable high-speed and highly accurate spectroscopic measurement (measurement of the structure, the film thickness, and the like) in the highly sensitive DUV-UV (190 to 400 nm) region.

DESCRIPTION OF EMBODIMENTS

Hereinafter, embodiments of the present invention will be described in detail with reference to the accompanying drawings. Note that components having the same function are denoted by the same reference symbols throughout the drawings for describing the embodiments, and the repetitive description thereof is omitted.

First Embodiment

First, a spectroscopic optical system which is an embodiment of the present invention will be described with reference to FIGS. 1 and 2.

Figure 1:
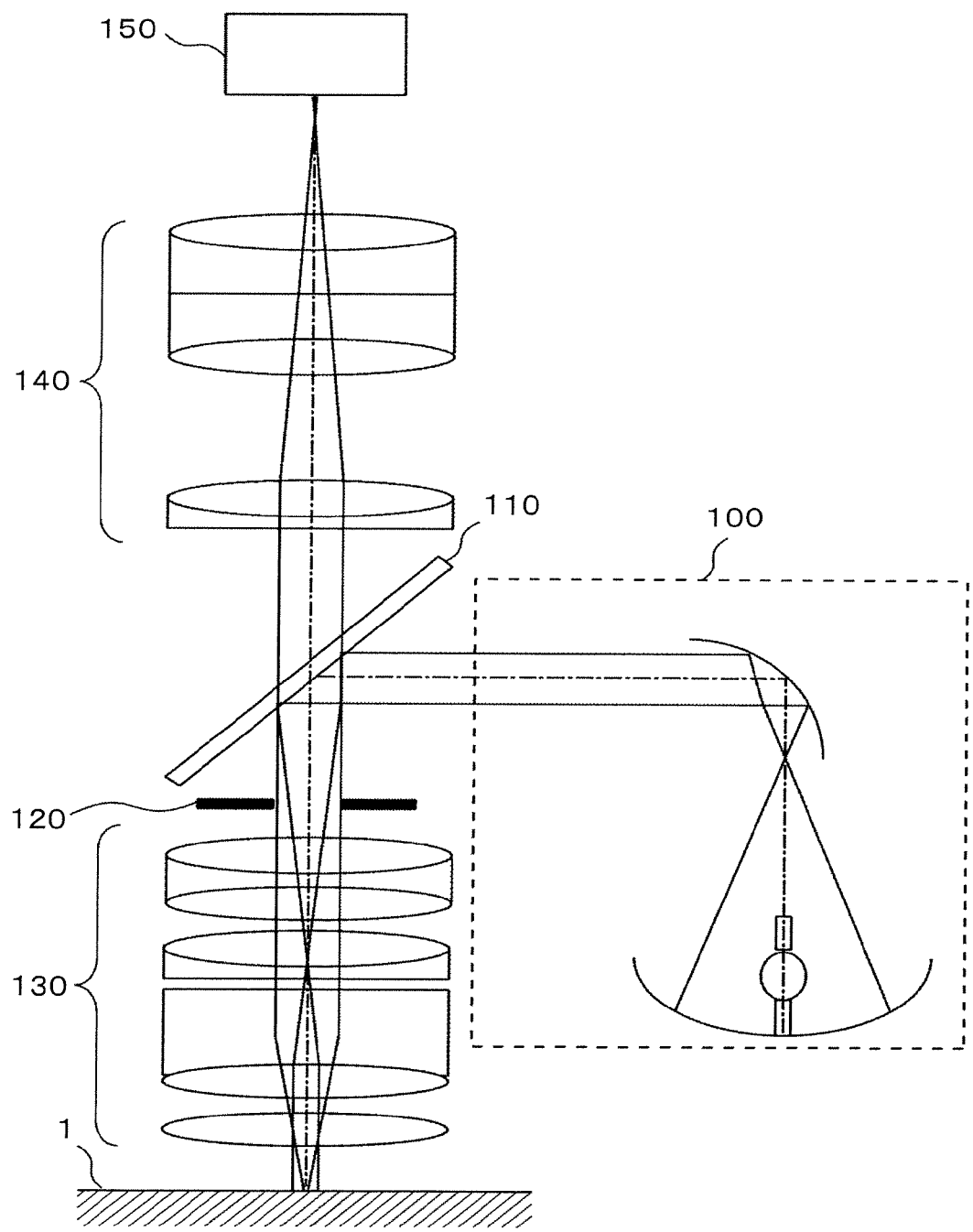
FIG. 1 is a diagram showing an example of the configuration of a spectroscopic optical system according to an embodiment of the present invention.

FIG. 1 is a diagram showing an example of the configuration of a spectroscopic optical system which is an embodiment of the present invention. The spectroscopic optical system includes an illumination optical system and a detection optical system.

The illumination optical system is configured to vertically illuminate a sample 1 on a stage, through a light source 100 for emitting illumination light, a folding member 110, a field stop 120, and an object-side objective lens system 130.

Similarly, the detection optical system is configured to vertically illuminate a spectroscope 150 for separating the specularly reflected light from the surface of the sample 1, through the object-side objective lens system 130, the field stop 120, the folding mirror 110, and an image-side focusing lens system 140 disposed on the image forming plane on the object side. It is to be noted that the surface of the sample 1 and the incident surface of the spectroscope 150 are conjugate to each other.

Figure 2A:
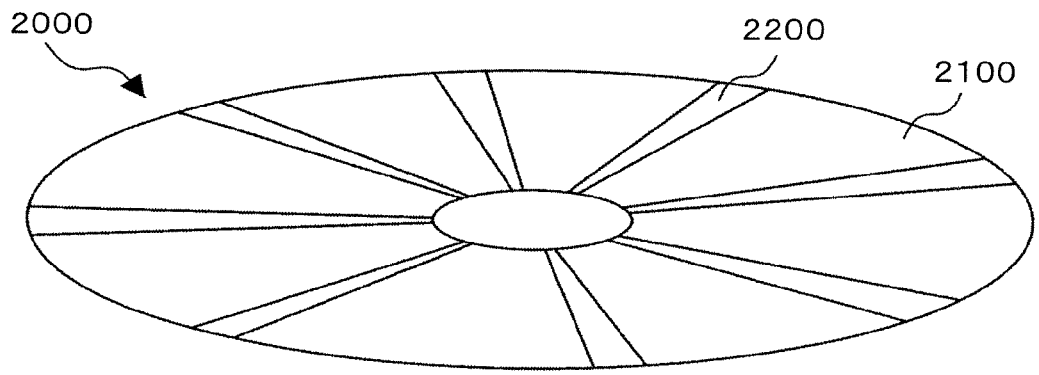
FIG. 2A is a schematic perspective view of a patterned media used as a sample in an embodiment of the present invention.

FIG. 2A is a schematic perspective view of a patterned media used as the sample 1. A patterned media 2000 is a recording medium in which magnetic particles are arranged artificially and regularly on a disk. An example of the patterned media 2000 is a magnetic recording medium used for hard disk devices. For example, on the surface of the patterned media 2000, there are a data part 2100 for writing user data as well as a servo part 2200 for tracking control and data access control including a burst signal, address, and preamble. In FIG. 2A, the arrangement of the data part 2100 and the servo part 2200 on the disk surface is schematically shown by the lines.

Figure 2B:
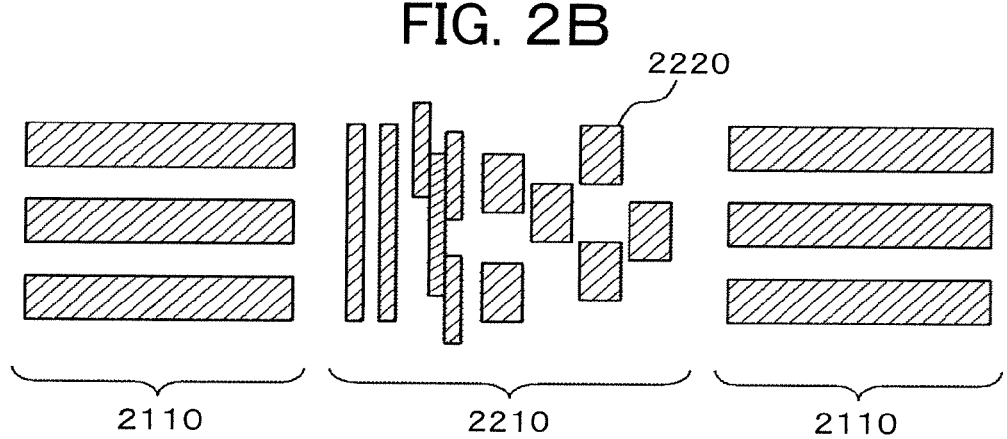
FIG. 2B and FIG. 2C are enlarged plan views of examples of the patterns of data part and servo part in the patterned media.

FIG. 2B is an enlarged plan view showing examples of patterns of the data part 2100 and the servo part 2200 in the patterned media 2000 shown in FIG. 2A. In a servo part 2210 of FIG. 2B, magnetic thin film patterns on the convex portions of a substrate with a concave-convex surface, correspond to servo patterns of the patterned media 2000. The servo part 2210 includes a burst signal 2220 for tracking control. In a data part 2110, a magnetic thin film is divided by the concave portions to form continuous tracks in the circumferential direction. The patterned media 2000 of this type is called discrete track media.

Figure 2C:
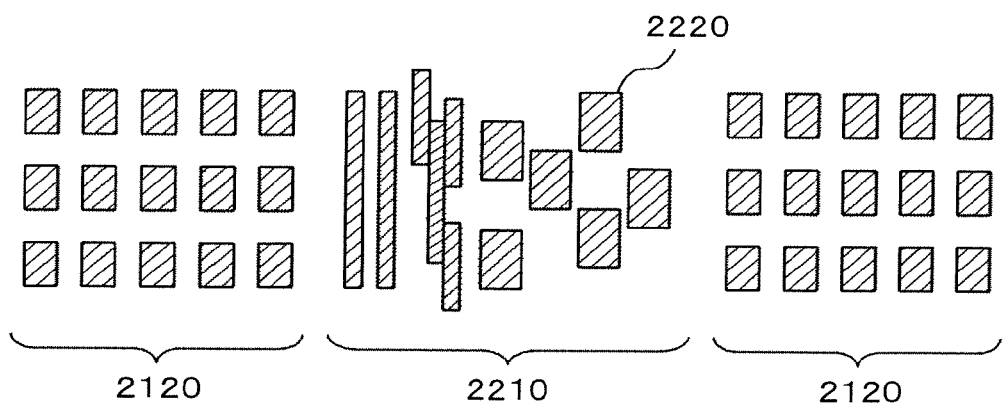

Similarly, FIG. 2C is an enlarged plan view showing examples of patterns of the data part 2100 and the servo part 2200 in the patterned media 2000 shown in FIG. 2A. In a data part 2120 of FIG. 2C, a magnetic thin film is divided by the concave portions to form data bits. The patterned media 2000 of this type is called bit patterned media.

Figure 3:
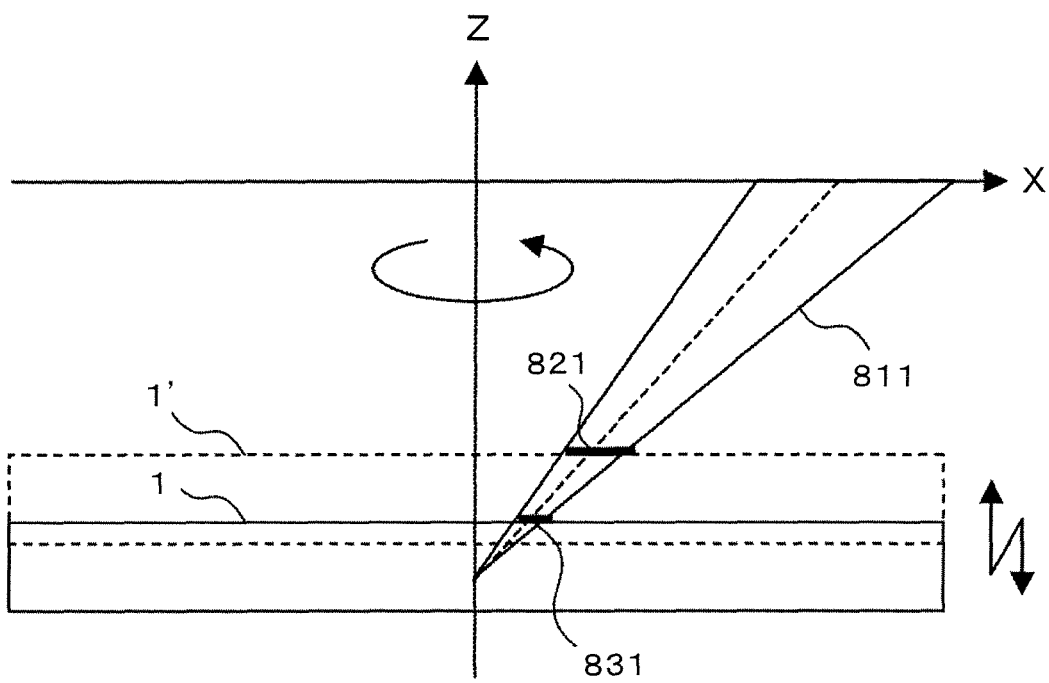
FIG. 3 shows the state in which displacement occurs due to vertical movement of the sample surface in the case of oblique illumination.
Figure 3:
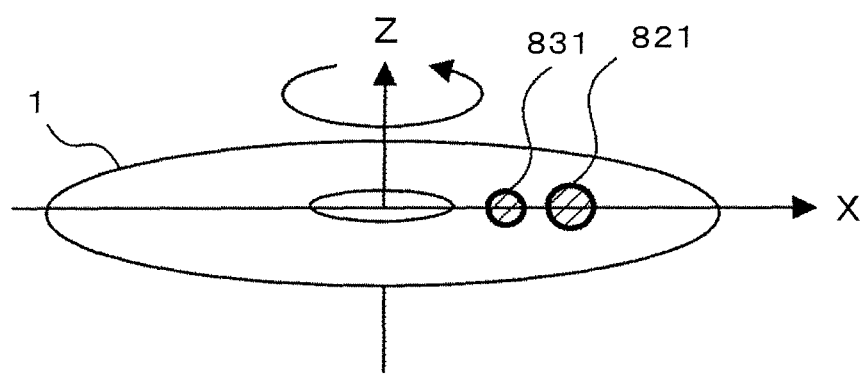
Figure 4:
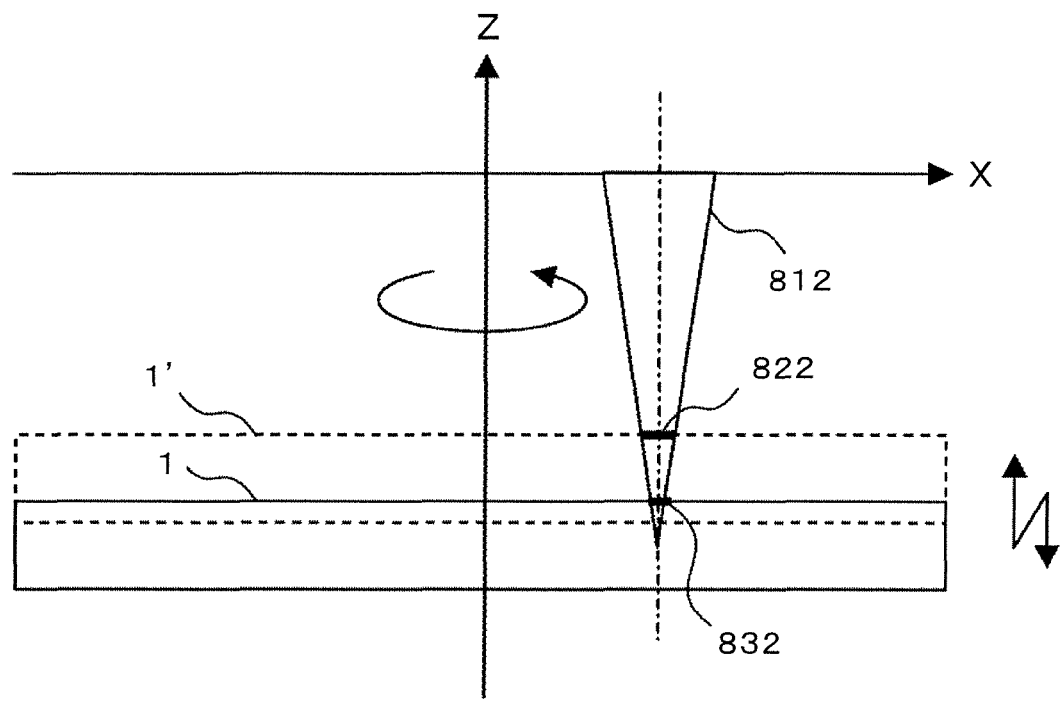
FIG. 4 shows the state in which displacement due to vertical movement of the sample surface is reduced in the case of vertical epi-illumination.
Figure 4:
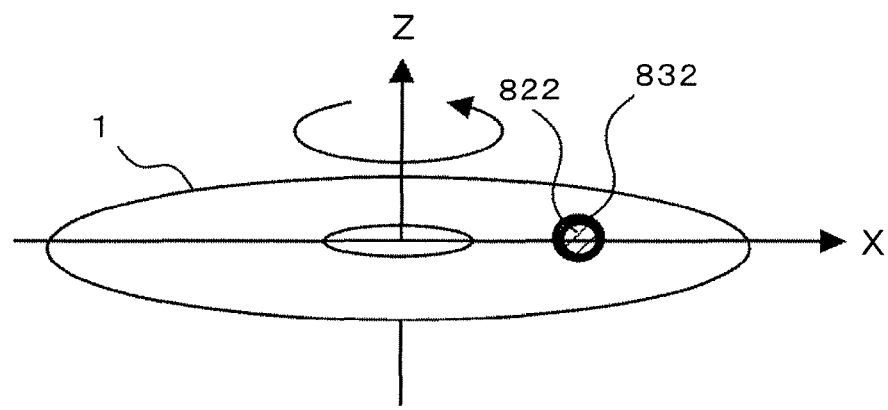

The data part 2100 and the servo part 2200 must be separated from each other. The reason is that when the sample surface is inspected by illuminating the data part 2100 with light to detect a spectral waveform, an accurate spectral waveform may not be detected when the light spot enters the servo part 2200. In particular, in the case of oblique illumination shown in FIG. 3, when the entire surface of the data part 2100 of the patterned media 2000 is continuously scanned, the surface of the sample 1 moves vertically. As a result, scan target positions 821, 831 are displaced and are very likely to enter the servo part 2200.

Next, the principle of chromatic aberration correction of the spectroscopic optical system will be described with reference to FIGS. 5 to 7.

First, the principle of the optical system for correcting chromatic aberration will be described with reference to FIG. 5. Achromatization of object points to converge different color lights into one point by a lens system can be expressed by the following equation (1).

Equation 1

$$\Delta s = \left(\frac{s_N}{h_N}\right)^2 \sum_{i=1}^{N} \cdot \frac{h_i^2 \phi_i}{v_i} \quad (1)$$

Figure 5:
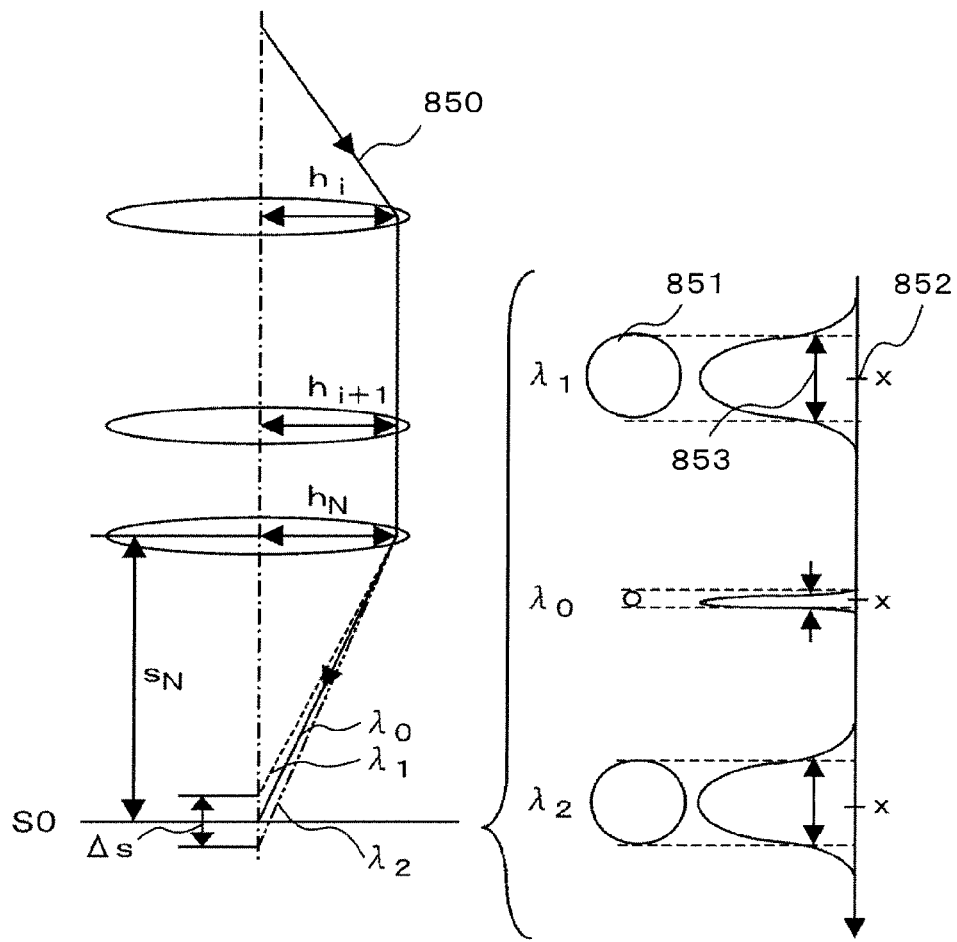
FIG. 5 is a diagram showing the principle of chromatic aberration correction and the method of calculating illumination width.
Figure 6:
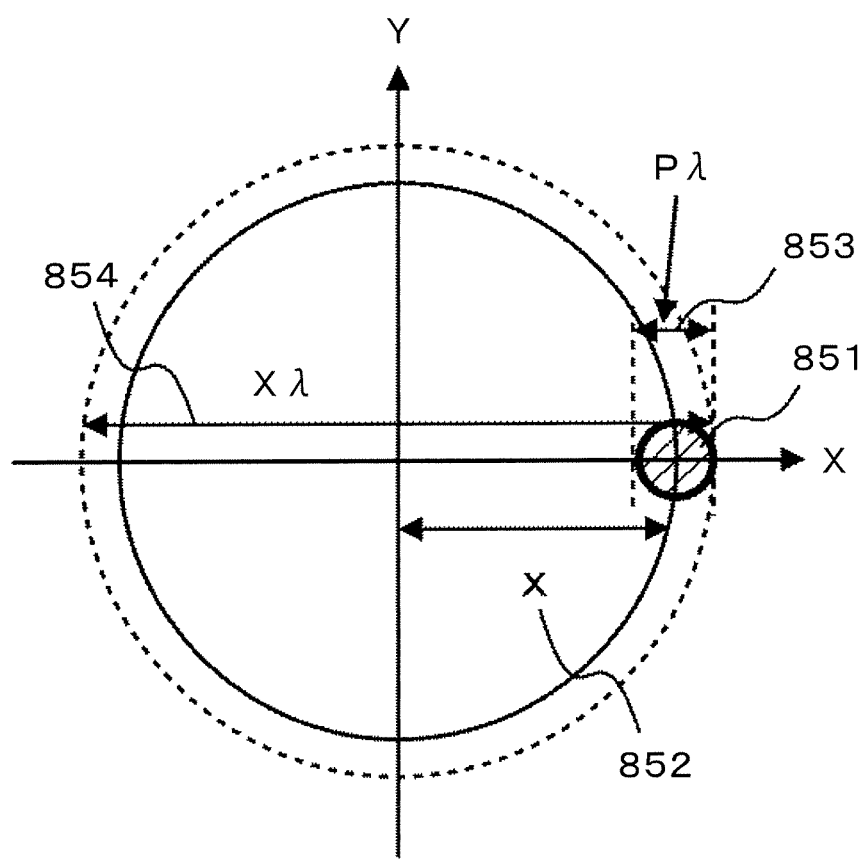
FIG. 6 is a diagram showing the method of calculating illumination width.

Here, as shown in FIG. 5, it is assumed that the number of lenses is N, the marginal ray height of each lens is hi, the marginal ray height of the last lens is hN, the distance from the last lens surface to the object surface is SN, and the refractive power and Abbe number of each lens are ϕi and vi, respectively. Further, the refractive power ϕi of each lens surface can be calculated from the lens surface curvature radius r and from the difference between the refractive indices n(λ) on the two sides thereof. The Abbe number vi can be calculated from the refractive indices of the center wavelength λ0, the short wavelength λ1, and the long wavelength λ2. In this way, the chromatic aberration ΔS is derived.

Further, the marginal ray height hi of each lens is substantially equal to the marginal ray height hN of the last lens. In other words, these rays are substantially parallel to each other. Thus, the equation (1) can be expressed by the following equation (2).

Equation 2

$$\Delta s = (s_N)^2 \sum_{i=1}^{N} \cdot \frac{\phi_i}{v_i} \quad (h_i \approx h_N) \quad (2)$$

The chromatic aberration can be reduced by reducing ΔS. In other words, the chromatic aberration can be reduced by reducing Σ(ϕi/vi), or reducing the distance SN from the last lens surface to the object surface. In the former case, the reduction can be achieved by adjusting the curvature radius, thickness, and space of the individual lenses. In the latter case, the reduction can be achieved by reducing the working distance (WD) of each lens.

Figure 7A:
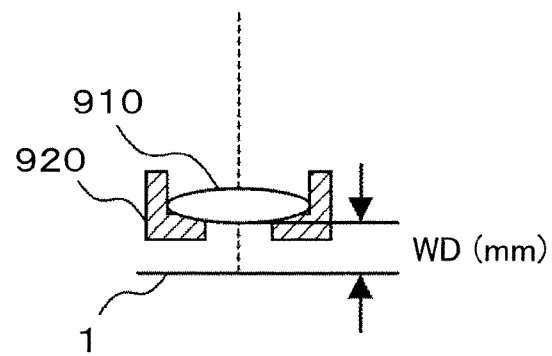
FIG. 7A is a diagram showing the working distance (WD) in which a lens as well as a lens barrel for accommodating the lens are taken into account.

FIG. 7 shows the color shift when the surface distance (WD) between the sample 1 and a lens 910 is reduced.

The color shift is the difference in an illumination width 854 of each wavelength in a surface S0 that is perpendicular to the optical axis. As shown in FIGS. 5 and 6, the calculation method of the difference in the illumination width 854 of each wavelength in the surface S0 is as follows.

First, a position 852 and an RMS value 853 are calculated by ray tracing with respect to the outermost image forming spot 851 in the surface S0 that is perpendicular to the optical axis.

Next, the illumination width 854 is given by the following equation (3) based on the position 852 and the RMS value 853 with respect to the image forming spot 851.

Equation (3)

$$X\lambda = 2 \cdot x + P\lambda \quad (3)$$

Here, Xλ is the illumination width, x is the position of the image forming spot, and Pλ is the RMS value.

The above calculation is performed for each wavelength.

Finally, the color shift is defined by the following equation (4) based on the illumination width 854 of each wavelength.

Equation (4)

$$\Delta x = \frac{\text{Max.}(X\lambda) - \text{Min.}(X\lambda)}{2 \times \text{Ave.}(X\lambda)} \times 100(\%) \quad (4)$$

Here, $\Delta x$ is the color shift (%) of each wavelength, Max. ($X\lambda$) is the largest illumination width of the wavelengths $\lambda$, Min. ($X\lambda$) is the smallest illumination width of the wavelengths $\lambda$, Ave. ($X\lambda$) is the average illumination width of the wavelengths $\lambda$. At this time, it is divided by 2 because the color shift of the wavelength is estimated for one side.

Figure 7B:
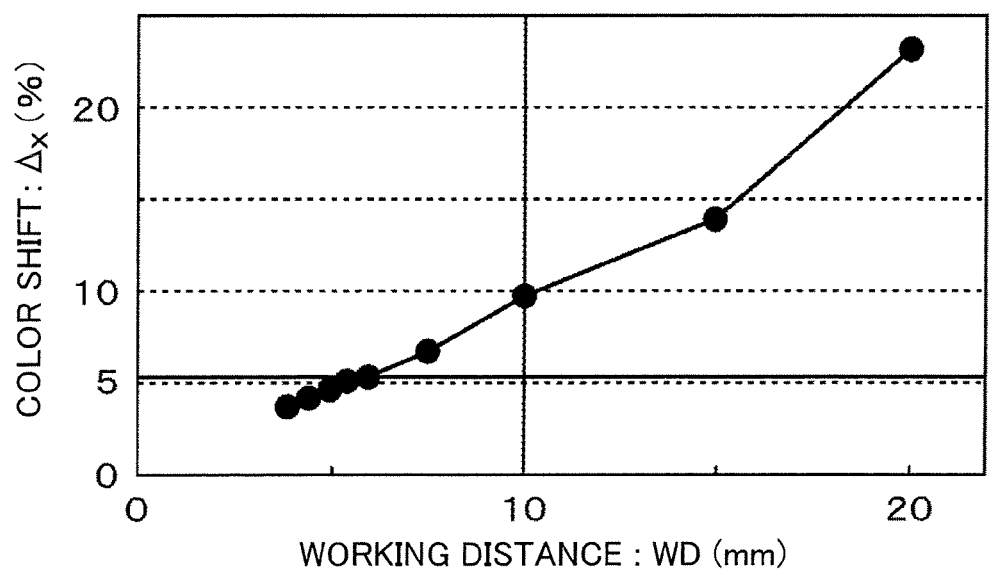
FIG. 7B is a diagram showing the relationship between the working distance (WD) and the color shift ($\Delta x$).

FIG. 7B shows the simulation result of plotting the color shifts of the individual wavelengths calculated as described above, with the surface distance (WD) being reduced. As a result, the color shift can be 10% or less by setting WD≤10.0 mm. At this time, the lower limit of WD≤10.0 mm is defined by the limit value for the implementation such as the lens barrel 920. The color shift is significantly increased with WD≥10.0 mm.

Next to be discussed using FIGS. 8 to 11 is uneven brightness (irregularity in the amount of light) due to interference, caused by lens attachment or thin spacer insertion when the UV curing agent (adhesive) is not used.

Figure 8:
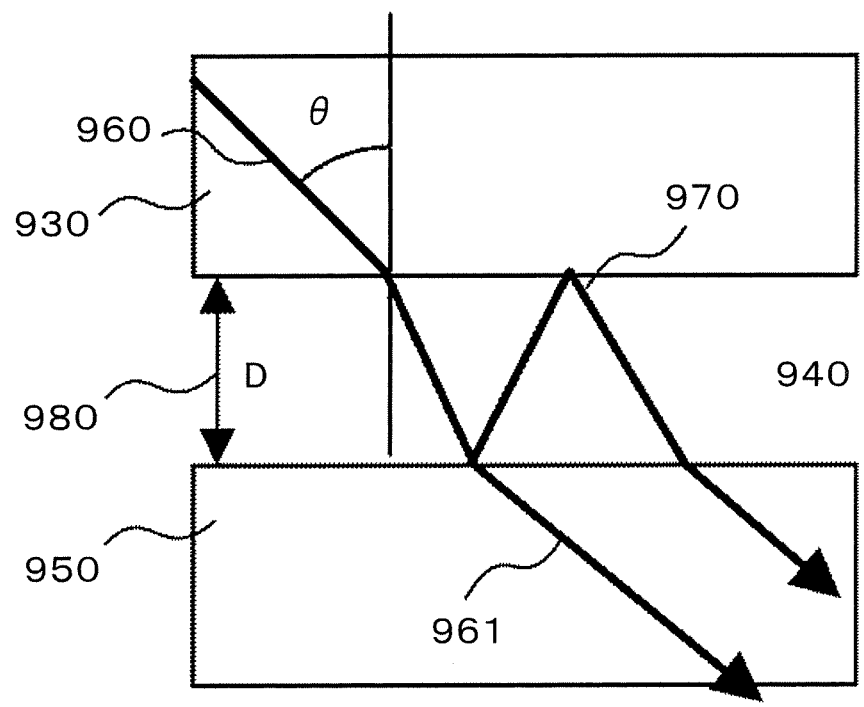
FIG. 8 is a diagram showing the principle of uneven brightness (irregularity in the amount of light) due to interference caused by the air space D between two lenses.

As shown in FIG. 8, a ray of light 960 is incident at an angle $\theta$ to the surface of a first lens 930, which includes a transmitted light 961 through a second lens 950, and a reflected light 970. In particular, the reflected light 970 after being transmitted through the first lens 930 is reflected on the surfaces of the second lens 950 and the first lens 930. Then, the reflected light 970 is transmitted through the second lens 950. Thus, there is a difference in the optical path length between the transmitted light 961 and the reflected light 970 depending on the air space 980. At this time, uneven brightness (irregularity in the amount of light) occurs due to interference, which is expressed by the following equation (5) in the case of multiple reflections.

Equation 5

$$I = (E_t)^2 = (E_{t1} + E_{t2} + E_{t3} + \dots)^2 \quad (5)$$

Here, I is the intensity, Et is the transmitted light amplitude, Et1 is the amplitude of the transmitted light 961 through the second lens 950, and Et2 is the amplitude of the transmitted light 970 through the second lens 950 after reflection (one reflection) on the surface of the first lens 930. In the case of multiple reflections, it continues with transmitted light amplitudes Et3, Et4, and so on.

When considering two-beam interference, the transmitted light 961 through the second lens 950 and the reflected light 970 have an optical path length difference $\Delta$ given by the following equation (6).

Equation (6)

$$\Delta = 2nD\cos\theta \quad (6)$$

Here, it is assumed that n is the refractive index of air, and $\theta$ is the incident angle.

Further, a phase difference $\delta$ of $\pi$ occurs between the transmitted light 961 through the second lens 950 and the reflected light 970, which can be expressed by the following equation (7).

Equation (7)

$$\delta = \frac{2\pi}{\lambda}\Delta + \pi \quad (7)$$

Here, $\Delta$ is the optical path length difference, and $\lambda$ is the wavelength.

By using the equations (5) and (7), the following equation (8) of two-beam interference can be obtained.

Equation (8)

$$I = (E_t)^2 = (E_{t1} + E_{t2})^2 = E_{t1}^2 + E_{t2}^2 + 2E_{t1}E_{t2}\cos\delta \quad (8)$$

Here, I is the transmitted light intensity of two-beam interference, Et is the transmitted light amplitude, Et1 is the amplitude of the transmitted light 961 through the second lens 950, and Et2 is the amplitude of the transmitted light 970 through the second lens 950 after reflections (two reflections) on the surfaces of the second lens 950 and the first lens 930. The degree of uneven brightness (irregularity in the amount of light) due to interference is dependent on the phase difference $\delta$.

The optical path length difference $\Delta$ given by the equation (6) has the phase difference of $\pi$. Thus, the brightness variation due to interference can be expressed as the following equation (9).

Equation (9)

$$\Delta = 2nD\cos\theta = 2m \cdot \frac{\lambda_1}{2} = (2m+1) \cdot \frac{\lambda_2}{2} \quad (9)$$

Here, the wavelength $\lambda_2$ is the target wavelength, and $\lambda_1$ is the result of adding the spectroscopic resolution $\gamma$ to the target wavelength $\lambda_2$. At this time, the longest wavelength of all the wavelengths in the range to be studied is selected as the wavelength $\lambda_2$. This is because the value D increases as the wavelength becomes longer.

The following equations (10), (11), and (12) can be derived from the equation (9).

Equation (10)

$$2m \cdot \frac{\lambda_1}{2} = (2m+1) \cdot \frac{\lambda_2}{2} \quad (10)$$

Equation (11)

$$2m \cdot (\lambda_1 - \lambda_2) = \lambda_2 \quad (11)$$

Equation (12)

$$\gamma = \lambda_1 - \lambda_2 = \frac{\lambda_2}{2m} \quad (12)$$

Here, the difference between the wavelengths $\lambda_1$ and $\lambda_2$ can be defined as the spectroscopic resolution $\gamma$. The spectroscopic resolution $\gamma$ and the integer value m are inversely related. The following equation (13) for calculating the air space D is derived by substituting the equation (12) into the equation (9).

Equation (13)

$$D = \frac{\lambda_1 \lambda_2}{4n\gamma\cos\theta} \quad (13)$$

The spectroscopic resolution $\gamma$ and the air space D are inversely related. Thus, when the spectroscopic resolution $\gamma$ is large, the air space D becomes small. On the other hand, when the spectroscopic resolution γ is small, the air space D becomes large.

For example, the air space D with a spectroscopic resolution γ of 1.0 nm will be discussed. At this time it is assumed that the wavelength range is 200 to 400 nm. Further, as the spectroscopic resolution γ is 1.0 nm, the target wavelengths are set to (1) 200±0.25, 0.50 nm, (2) 300±0.25, 0.50 nm, and (3) 400±0.25, 0.50 nm, respectively. The transmittance in the air space D for each wavelength will be discussed below.

Figure 9A:
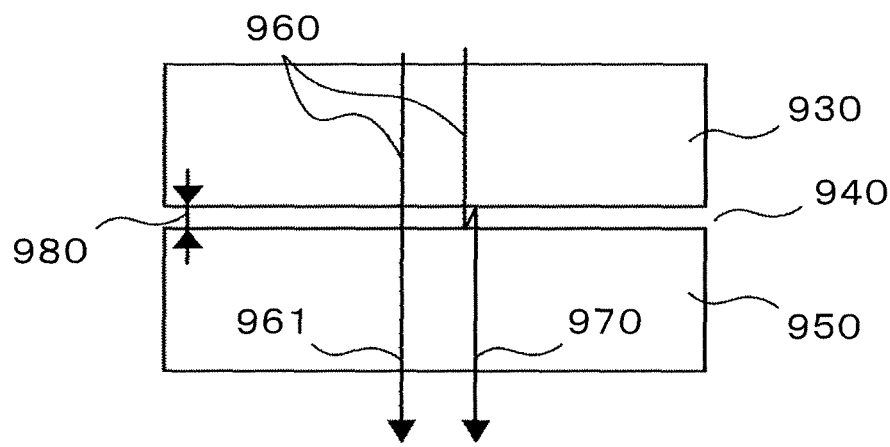
FIG. 9A is a schematic diagram in which the air space D between two lenses is set from 0 to 0.5 μm.

It is assumed a structure having the first lens 930, the second lens 950, and an air layer 940 as shown in FIG. 9A. The light 960, which is incident at an angle θ to the surface of the first lens 930, includes the transmitted light 961 through the second lens 950, and the transmitted light 970 after reflection on the surface of the second lens 950. A discussion will be made on the transmittance with respect to these two lights when the air space D 980 is changed from 0 to 0.5 μm. Here, the wavelengths are set to (1) 200 nm, (2) 300 nm, and (3) 400 nm, respectively.

Figure 9B:
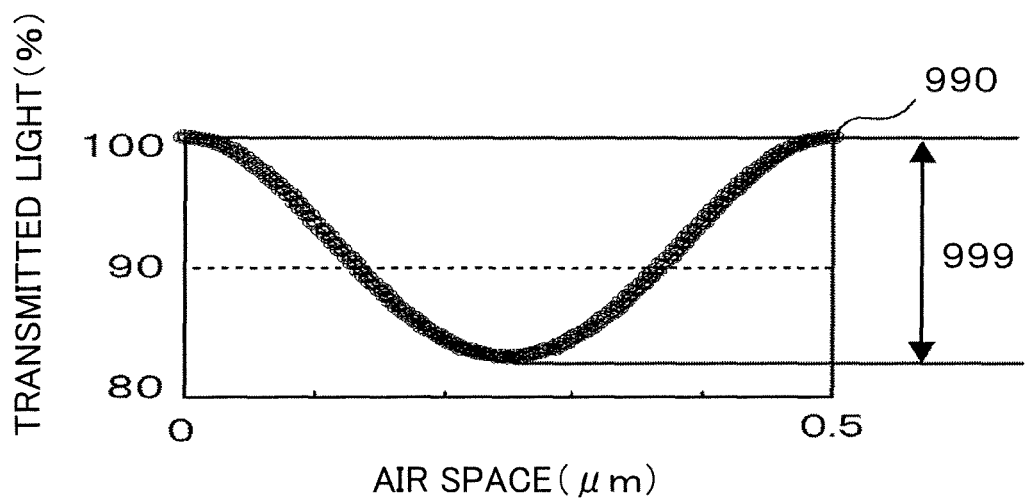
FIG. 9B is a graph of simulation results of the transmittance at wavelengths from 199.50 to 200.50 nm when the air space D is changed from 0 to 0.5 μm.

FIG. 9B shows the simulation result of the transmittance at the wavelength (1) 200 nm when the air space D 980 is changed from 0 to 0.5 μm. The wavelengths of transmittance waveforms shown in FIG. 9B are 199.50 nm, 199.75 nm, 200.00 nm, 200.25 nm, and 200.50 nm. It is also shown an average 990 of the transmittance waveforms of the respective wavelengths. As a result, it is found that when the air space D 980 is small in the range of 0 to 0.5 μm, the waveform phases of all the wavelengths are the same and uneven brightness (irregularity in the amount of light) occurs at the average 990. This is because the air space D 980 is so small that the optical path length difference hardly occurs between the transmitted light 961 and the transmitted light 970 after reflection, so that mutual cancelling effect is not applied.

Figure 10A:
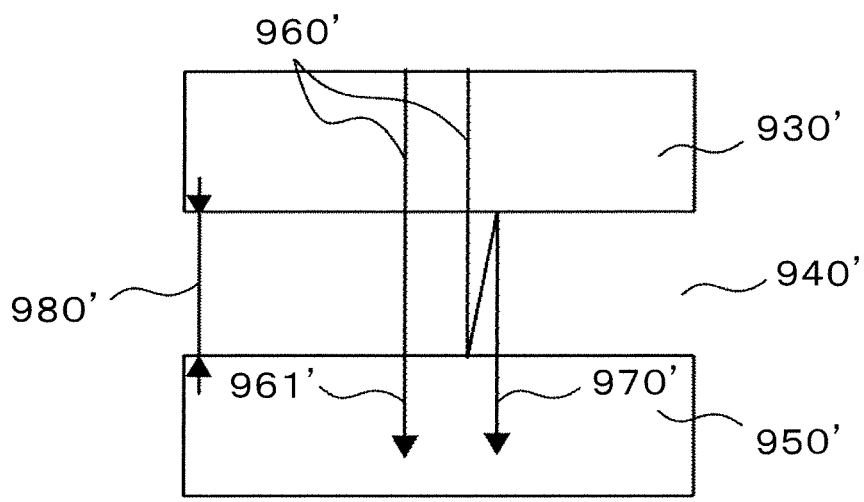
FIG. 10A is a schematic diagram of the case in which the air space D between two lenses is set from 30 to 30.1

A discussion will be made on the transmittance with respect to the two lights shown in FIG. 10A when an air space D 980' is changed from 30 to 30.1 μm. Here, the wavelengths are set to (1) 200 nm, (2) 300 nm, and (3) 400 nm, respectively.

Figure 10B:
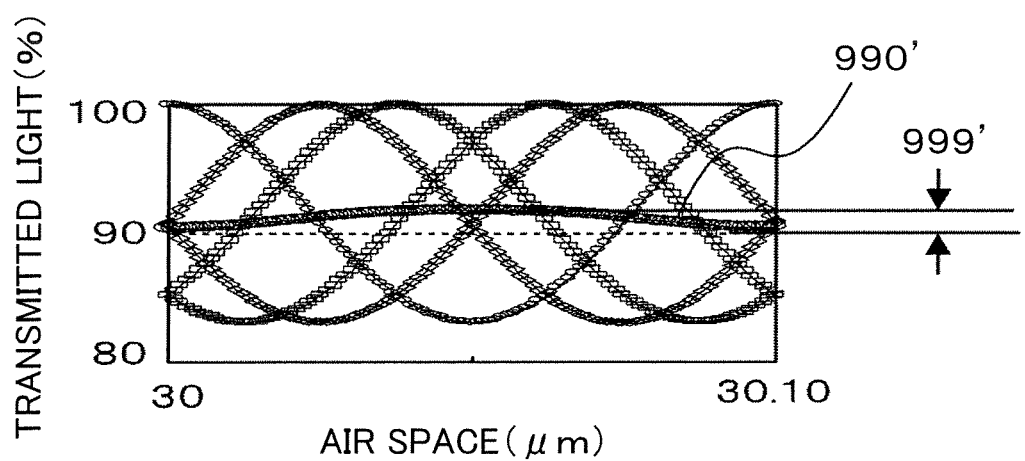
FIG. 10B is a graph of simulation results of the transmittance at wavelengths from 199.50 to 200.50 nm when the air space D is changed from 30 to 30.1 μm.

FIG. 10B shows the simulation result of the transmittance at the wavelength (1) 200 nm when the air space D 980' is increased to 30 μm and changed from 30 to 30.1 μm. The wavelengths of transmittance waveforms shown in FIG. 10B are 199.50 nm, 199.75 nm, 200.00 nm, 200.25 nm, and 200.50 nm, respectively. It is also shown an average 990' of the transmittance waveforms of the respective wavelengths. As a result, it is found that when the air space D 980' is large in the range of 30 to 30.1 μm, the waveform phases of the individual wavelengths are shifted and uneven brightness (irregularity in the amount of light) is reduced and equalized at the average 990'. This is because the air space D 980' is so large that the optical path difference occurs between a transmitted light 961' and a transmitted light 970' after reflection, so that mutual cancellation is applied.

When assuming that the wavelength λ1=401 nm, the wavelength λ2=400 nm, the spectroscopic resolution γ=1.0 nm, the incident angle θ=0° (vertical incidence), and the air refraction index n is substantially equal to 1, the air space D must satisfy D≥40.1 μm from the equation (13). When the air space D does not satisfy D≥40.1 μm, there is little difference in the optical path length between the transmitted light 961 and the transmitted light 970 after reflection. The mutual cancellation is not applied. As a result, uneven brightness (irregularity in the amount of light) occurs.

Figure 11A:
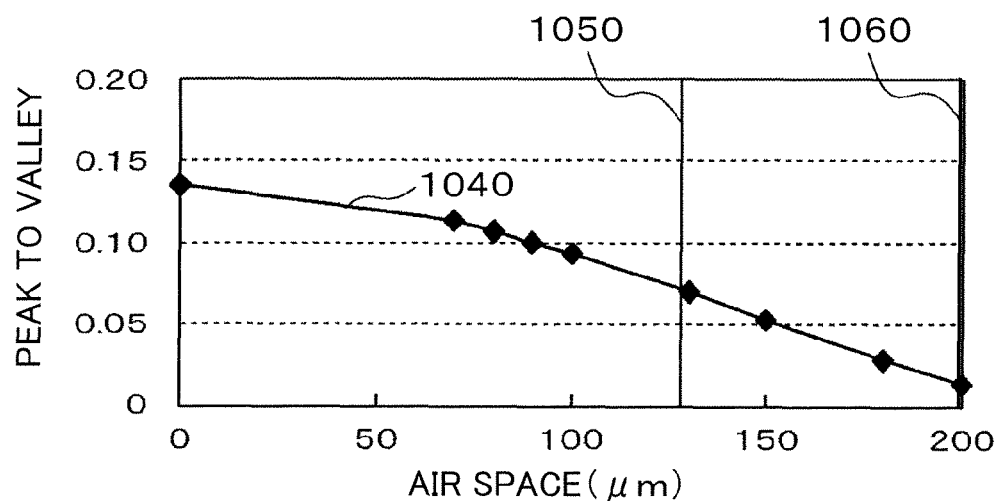
FIG. 11A is a graph plotting Peak to Valley values of the transmittance with a spectrometer resolution $\gamma=0.3$ nm at a wavelength of 400 nm, for each air space D.

FIG. 11A is a graph plotting a Peak to Valley value 999 of the transmittance waveform with the spectroscopic resolution γ=0.3 nm at the wavelength=400 nm, for each air space D.

Figure 11B:
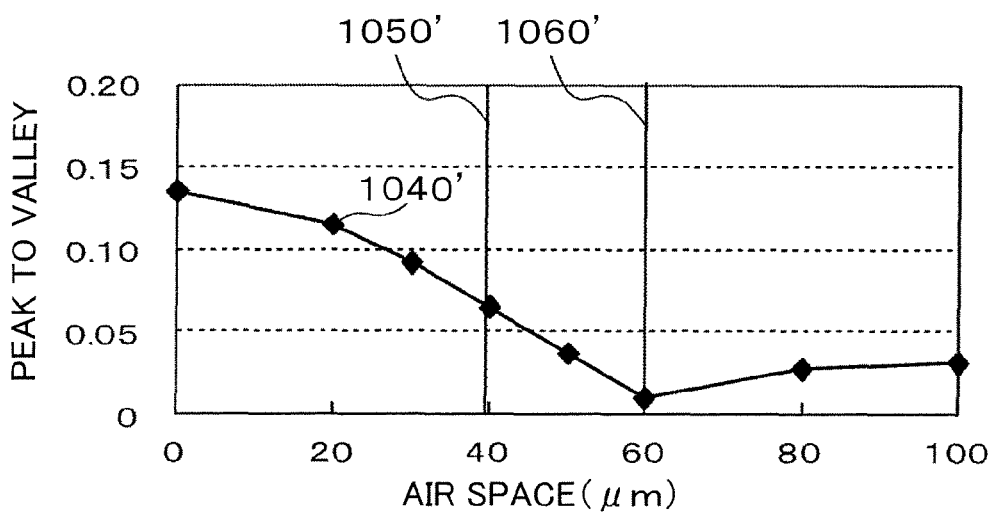
FIG. 11B is a graph plotting Peak to Valley values of the transmittance with a spectrometer resolution $\gamma=1.0$ nm at a wavelength of 400 nm, for each air space D.

FIG. 11B is a graph plotting a Peak to Valley value 999' of the transmittance waveform with the spectroscopic resolution γ=1.0 nm at the wavelength=400 nm, for each air space D.

When the spectroscopic resolution γ is 0.3 nm, the air space D must satisfy D≥133.4 μm from the equation (13). When the air space D does not satisfy D≥133.4 μm, there is little difference in the optical path length between the transmitted light 961 and the transmitted light 970 after reflection. The mutual cancellation is not applied. As a result, uneven brightness (irregularity in the amount of light) occurs.

There is a mismatch between the simulation results 1040, 1040' shown in FIG. 11, and the results 1050, 1050' of the equation (13). This is because only one reflection is taken into account in the equation (13), although actually with multiple reflections. Thus, it is necessary to multiply 1.5 times the air space D calculated by the equation (13) to obtain 1060, 1060'.

Second Embodiment

Figure 12:
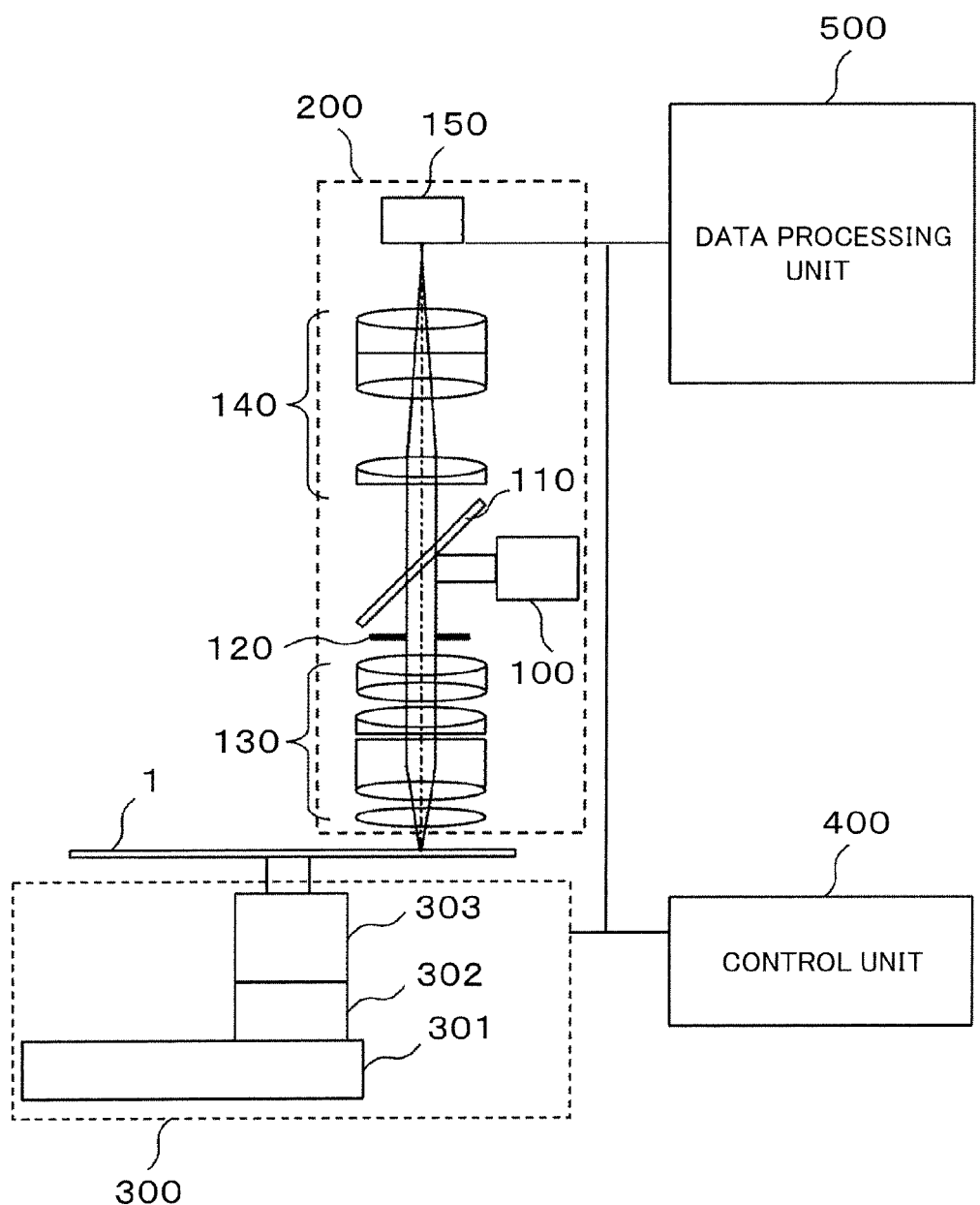
FIG. 12 is a diagram showing an example of the configuration of a hard disk detection device using the spectroscopic optical system which is an embodiment of the present invention.

Hereinafter a hard disk inspection device will be described as an example of the spectrometer using the spectroscopic optical system according to this embodiment. FIG. 12 is a diagram showing an example of the configuration of a hard disk inspection device using the spectroscopic optical system according to this embodiment.

The hard disk inspection device includes: a spectroscopic optical system 200 for illuminating the sample 1 with light to separate and detect specularly reflected light from the sample 1; a stage part 300 on which the sample 1 is placed, capable of moving the position of the sample 1 relative to the spectroscopic optical system 200; a control unit 400 for controlling the operation of the spectroscope 150 and the stage part 300; and a data processing unit 500 for detecting the shape or abnormal shape of patterns formed on the sample 1 based on the spectral waveform data detected by the spectroscope.

The spectroscopic optical system 200 has the same configuration as the spectroscopic optical system shown in FIG. 1. At this time, when the entrance position of the spectroscope 150 is defined as the image forming position, it is possible to control the size of the area to be spectroscopically surveyed in the sample 1 by the size of the entrance of the spectroscope 150. For example, the size of the entrance is set to φ400 μm and the magnification on the image forming plane is set to ×8. In this case, the size of the spectroscopically surveyed area is φ50 μm on the target disk (sample 1).

As described above, when the wavelength around 400 nm is used, the types of optical devices and the like that can be applied are limited. Examples of the light source 100 are xenon and deuterium lamps that emit light at a wavelength of about 190 nm or more. However, depending on the sample 1, it is also possible to achieve sufficient performance with a wavelength of about 400 nm or more. In such a case, a halogen lamp or other light source that emits light from visible to infrared can be used as the light source 100.

Finally, a description will be given of the stage part 300, the control unit 400, and the data processing unit 500 in the hard disk inspection device according to this embodiment. In FIG. 12, the stage part 300 includes an X stage 301 for moving in the direction perpendicular to the surface of the sample 1, a Z stage 302 for moving in the direction perpendicular to the surface of the sample 1, and a θ stage 303 for rotating the disk (patterned media 2000) of the sample 1. The Z stage 302 causes the sample 1 to move to the focal position of the spectroscopic optical system 200. The X stage 301 and the θ stage 303 cause the spectroscopic optical system 200 to move to any position on the sample 1.

Further, an XY stage can be used as a method of moving the spectroscopic optical system to any position on the sample 1. An Xθ stage is more appropriate than the XY stage when the sample 1 is a disk and the pattern on the sample surface is formed concentrically. Also, the Xθ stage is more appropriate than the XY stage when it is desired to inspect the entire surface of the disk at high speed, because the operation is simpler with the Xθ stage than with XY stage. For this reason, the hard disk inspection device according to this embodiment has an Xθ stage structure using the X stage 301 and the θ stage 303.

Figure 13:
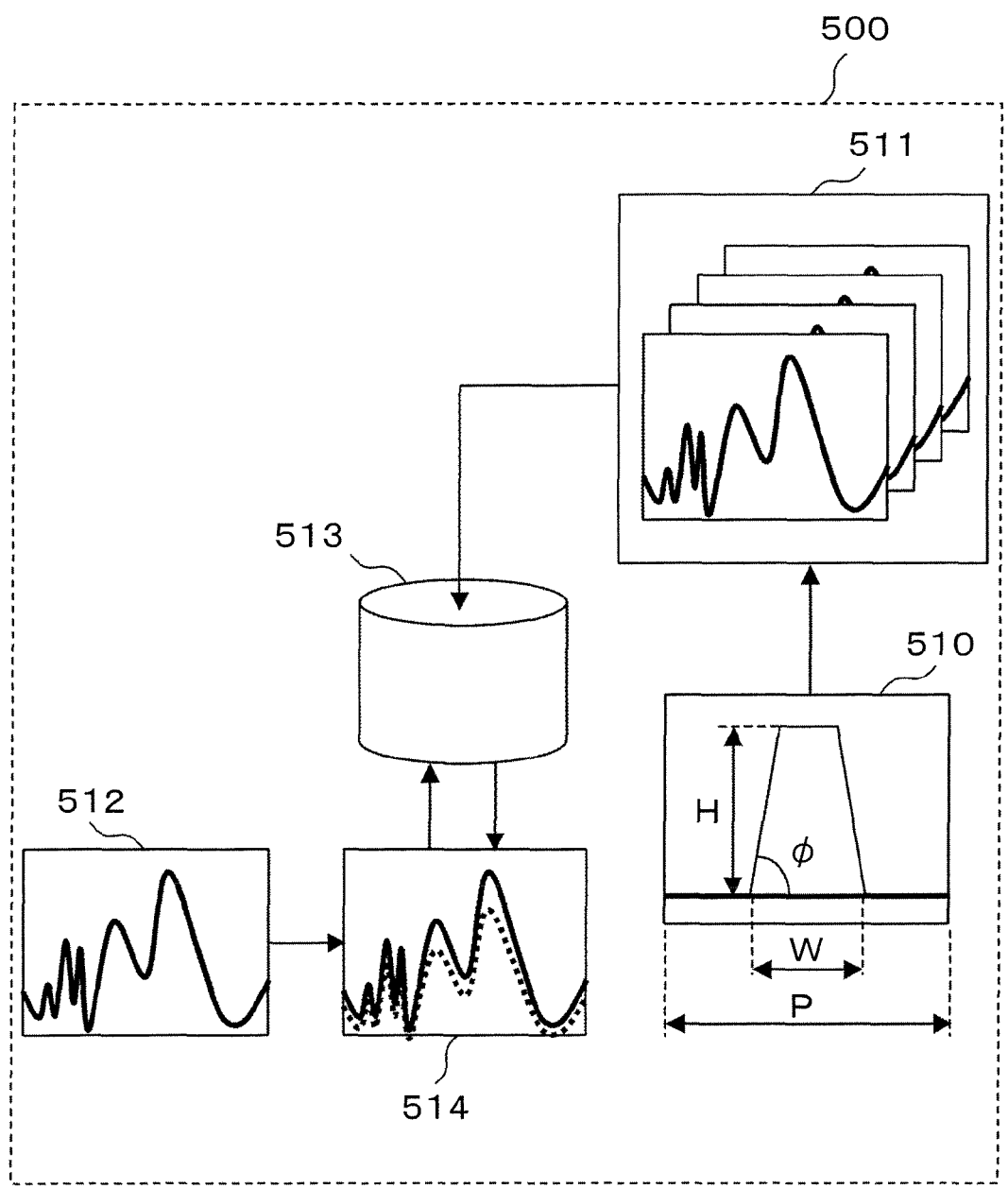
FIG. 13 is a schematic diagram showing the process of the data processing unit in an embodiment of the present invention.

FIG. 13 is a schematic diagram of the process in the data processing unit 500. The process of the data processing unit 500 is roughly divided into the following two processes. One is the spectral reflectance calculation, and the other is the pattern shape and defect detection process. As described above, in the hard disk inspection device according to this embodiment, the pattern shape and defects of the sample 1 are detected based on the spectral reflectance of the surface of the sample 1.

The spectroscopic optical system 200 can detect the spectral intensity distribution of the surface of the sample 1. Thus, optical simulation is applied to the sample 1 having a different pattern shape 510 in advance. Then, a graph 511 of the wavelength dependence of the calculated spectral reflectance is stored in a database 513. Next, the sample 1 on which the pattern is repeatedly formed is illuminated with light from the light source 100 through the spectroscopic optical system 200. In this way, the specularly reflected light from the sample surface is received by the spectroscope 150.

The data processing unit 500 obtains a graph 512 of the wavelength dependence of the spectral reflectance, based on the spectral intensity distribution detected by the spectroscope 150. Finally, an approximation to the graph 512 of the wavelength dependence of the spectral reflectance that is obtained by measurement, is selected from the graph 511 of the wavelength dependence of the spectral reflectance that is calculated by optical simulation and is stored in the database 513, by means of a comparison 514 of the waveforms of the spectral reflectance. In this way, the shape of the sample 1 can be identified.

As described above, the spectroscopic optical system 200 according to this embodiment includes: the illumination optical system including the light source 100, the folding mirror 110, the field stop 120, and the object-side objective lens system 130 for illuminating the sample 1; the detection optical system including the object-side objective lens system 130, the field stop 120, the folding mirror 110, and the image-side focusing lens system 140 disposed on the image forming plane of the sample 1; and the spectroscope 150 for separating the specularly reflected light from the sample 1. In this configuration, the object-side objective lens system 130 and the image-side focusing lens system 140 are color corrected in a wide range of deep ultraviolet to ultraviolet light at wavelengths of 190 to 400 nm. The object-side objective lens system 130 and the image-side focusing lens system 140 are formed only by refractive lenses.

At this time, when the working distance (WD) of each lens is set to WD≤10.0 mm, it is possible to reduce the color shift.

Further, when the distance D of each doublet is set to $(\lambda 1 \cdot \lambda 2)/(4n\gamma) \leq D$, it is possible to prevent the occurrence of uneven brightness (irregularity in the amount of light).

Still further, because the vertical epi-illumination is used, it is possible to reduce the displacement due to defocusing, which has been a problem in oblique illumination of the reflection optical system. In addition, the illumination positions of the individual wavelengths coincide by wide range color correction. Thus, highly accurate spectroscopic measurement (structure and film thickness measurement, and the like) can be achieved.

While the invention made by the present inventors has been described specifically based on its embodiments hereinbefore, it will be appreciated that the present invention is not limited to the embodiments and various modifications may be made without departing from the gist of the invention.

For example, the spectroscopic optical system 200 and the spectrometer according to this embodiment are designed to detect the pattern shape and defects on the surface of the patterned media 2000 by spectroscopic measurement. However, the sample 1 is not limited to the patterned media 2000. As long as the sample 1 has a structure and pattern on the surface, the data processing unit 500 can detect the structure by matching the spectral reflectance. Further, in addition to the detection of the surface structure of the sample 1, it is also possible to apply the measurement of the thin film thickness, and the like, by spectroscopic measurement.

Industrial Applicability

The spectroscopic optical system and the spectrometer according to the present invention can be applied to spectroscopic optical systems and spectrometers for performing wide range color correction by optical systems using refractive lenses, such as semiconductor and patterned media inspection devices, as well as thin film thickness measuring devices by spectroscopic measurement.

REFERENCE SIGNS LIST 1, 1': sample
100: light source
110: folding member
120: field stop
130: object-side objective lens system
140: image-side focusing lens system
150: spectroscope
200: spectroscopic optical system
300: stage part
301: X stage
302: Z stage
303: θ stage
400: control unit
500: data processing unit
510: pattern shape
511: graph of wavelength dependence of spectral reflectance calculated by simulation
512: graph of wavelength dependence of spectral reflectance based on the detected spectral intensity distribution
513: database
514: comparison of waveforms of spectral reflectance
811: oblique illumination
812: vertical illumination
821, 822: position to be scanned before defocusing
831, 832: position to be scanned after defocusing
850: marginal ray
851: outermost image forming spot
852: position x of the outermost image forming spot
853: RMS value Pλ of the outermost image forming spot
854: illumination width xλ
910: lens
920: lens barrel
930, 930': first lens
940, 940': air
950, 950': second lens
960, 960': incident light
861, 961': transmitted light through the second lens
970, 970': reflected light on the first and second lens surfaces
980, 980': air space D

990: transmittance waveforms at wavelengths of 199.50 nm, 199.75 nm, 200.00 nm, 200.25 nm, and 200.50 nm, and average of the transmittance waveforms from 199.50 to 200.50 nm

990': average of the transmittance waveforms from 199.50 to 200.50 nm

991': transmittance waveform of 199.50 nm

992: transmittance waveform of 199.75 nm

993': transmittance waveform of 200.00 nm

994': transmittance waveform of 200.25 nm

995': transmittance waveform of 200.50 nm

1040: plot of Peak to Valley values for each air space with respect to the average of the transmittance waveforms from 399.85 to 400.1 nm

1040': plot of Peak to Valley values for each air space with respect to the average of the transmittance waveforms from 399.50 to 400.50 nm

2000: patterned media

2100-2120: data part

2200-2210: servo part

2220: burst signal pattern

The invention claimed is:

1. A spectroscopic optical system comprising:
an illumination optical system including a light source, a folding mirror, a field stop, and an object-side objective lens system for illuminating a sample;
a detection optical system including the object-side objective lens system, the field stop, the folding mirror, and an image-side focusing lens system disposed on an image forming plane on the object side; and
a spectroscope for separating specularly reflected light from the sample, wherein:
the object-side objective lens system and the image-side focusing lens system are color corrected in a broad range of wavelengths from 190 to 400 nm, the two systems being formed only by refractive lenses, and
the working distance (WD) of each lens is set so as to satisfy the following equation (1):

$$WD \leq 10.0 \text{ mm}, \tag{1}$$

a distance D between each of the adjacent lenses within each doublet is set so as to satisfy the following equation (2):

$$(\lambda 1 - \lambda 2)/4n\gamma \leq D \tag{2}$$

n is a refractive index of air and $\gamma$ is a spectroscopic resolution, $\lambda 2$ is a wavelength to be studied, which is determined by selecting the longest wavelength of all the wavelengths in the range to be studied, and
$\lambda 1$ is obtained by adding the spectroscopic resolution y to the target wavelength $\lambda 2$.

2. The spectroscopic optical system according to claim 1, wherein the light source emits light in the deep ultraviolet to visible range.

3. The spectroscopic optical system according to claim 1, wherein the illumination optical system is designed to vertically illuminate the sample.

4. The spectroscopic optical system according to claim 1, wherein the object-side illumination optical system and the image-side detection optical system are formed only by refractive lenses of fluorite and quartz.

5. The spectroscopic optical system according to claim 1, wherein the distance D of each doublet is set to satisfy the following equation (3) by taking into account multiple reflections:

$$1.5 \cdot (\lambda 1 - \lambda 2)/(4n\gamma) \leq D \tag{3}$$

6. A spectrometer comprising:
the spectroscopic optical system according to claim 1;
a stage part on which the sample is placed, being capable of moving a position of the sample relative to the spectroscopic optical system;
a control unit for controlling the operation of the spectroscope and the stage part; and
a data processing unit for detecting a shape or abnormal shape of patterns formed on the sample, based on the spectral intensity distribution detected by the spectroscope.

7. The spectrometer according to claim 6, wherein the stage part causes the sample to move so that an entire surface of the sample is continuously scanned by the spectroscopic optical system.

8. The spectrometer according to claim 6, wherein the data processing unit has a database for storing graphs of the wavelength dependence of the spectral reflectance that is calculated in advance for a different pattern shape in the sample,
wherein the data processing unit obtains a graph of the wavelength dependence of the spectral reflectance that is measured for the sample, based on the spectral intensity distribution detected by the spectroscope, and
wherein the data processing unit identifies the pattern shape formed on the sample, by selecting the one that matches the graph of the wavelength dependence of the spectral reflectance that is measured for the sample, from the graphs of the wavelength dependence of the spectral reflectance, which are stored in the database, by means of comparison of the waveforms of the spectral reflectance.

9. The spectrometer according to claim 8, wherein the pattern shape includes the film thickness.

* * * * *